US009080975B2

(12) United States Patent
Gnauert

(10) Patent No.: US 9,080,975 B2
(45) Date of Patent: Jul. 14, 2015

(54) DEVICE AND METHOD FOR ASCERTAINING MEASURED VALUES OF GASES AND/OR AN AEROSOL FOR A MACHINE

(71) Applicant: Schaller-Automation Industrielle Automationstechnik GmbH & Co. KG, Blieskastel (DE)

(72) Inventor: Uwe Gnauert, Blieskastel (DE)

(73) Assignee: Schaller-Automation Industrielle Automationstechnik GmbH & Co. KG, Blieskastel (DE)

( * ) Notice: Subject to any disclaimer, the term of this patent is extended or adjusted under 35 U.S.C. 154(b) by 0 days.

(21) Appl. No.: 14/371,262

(22) PCT Filed: Nov. 19, 2012

(86) PCT No.: PCT/EP2012/073017
§ 371 (c)(1),
(2) Date: Jul. 9, 2014

(87) PCT Pub. No.: WO2013/104454
PCT Pub. Date: Jul. 18, 2013

(65) Prior Publication Data
US 2015/0000388 A1    Jan. 1, 2015

(30) Foreign Application Priority Data
Jan. 13, 2012   (EP) .................................... 12151046

(51) Int. Cl.
| | |
|---|---|
| *G01M 15/04* | (2006.01) |
| *G01N 21/59* | (2006.01) |
| *F01M 11/10* | (2006.01) |
| *F01M 13/02* | (2006.01) |
| *G01N 21/53* | (2006.01) |
| *G01N 33/28* | (2006.01) |
| *G01N 33/30* | (2006.01) |

(52) U.S. Cl.
CPC ............... *G01N 21/59* (2013.01); *F01M 11/10* (2013.01); *F01M 13/02* (2013.01); *F01M 13/021* (2013.01); *G01M 15/042* (2013.01); *G01N 21/534* (2013.01); *G01N 33/2888* (2013.01); *G01N 33/30* (2013.01); *F01M 2013/026* (2013.01); *G01N 2201/061* (2013.01); *G01N 2201/0636* (2013.01)

(58) Field of Classification Search
CPC ........................... G01M 15/04; G01M 15/042
USPC ................ 73/114.55, 114.56, 114.57, 114.71
See application file for complete search history.

(56) References Cited

U.S. PATENT DOCUMENTS

| | | | |
|---|---|---|---|
| 4,475,382 A | 10/1984 | Frank | |
| 6,137,582 A | 10/2000 | Stedham | |
| 2012/0291535 A1* | 11/2012 | Maloney et al. ............ | 73/114.57 |
| 2013/0125624 A1* | 5/2013 | Gnauert ....................... | 73/31.01 |

FOREIGN PATENT DOCUMENTS

| | | |
|---|---|---|
| DE | 26 08 390 A1 | 9/1977 |
| DE | 239 474 A | 9/1986 |

(Continued)

*Primary Examiner* — Eric S McCall
(74) *Attorney, Agent, or Firm* — George Pappas

(57) ABSTRACT

A measuring device (2) draws out an aerosol air mixture from the working chamber (4) of the machine and feeds it to an optical sensor unit with an optical emitter (15) and an optical receiver (17). A compressed air jet pump (8) includes a compressed air feed (26), a compressed air nozzle (32), a preferably funnel-shaped pressure discharge channel and an underpressure region (10), with the compressed air nozzle (32) having an outlet direction oriented substantially in the direction of the pressure discharge channel. The compressed air feed (26) is connected to a compressed air source. A suction line is connected between the working chamber (4) and the underpressure region (10). The optical sensor unit has an optical passage between the optical emitter (15) and the optical receiver (17) oriented substantially perpendicular to the outlet direction of the compressed air nozzle (32) and leads through the underpressure region.

20 Claims, 2 Drawing Sheets

(56) References Cited

FOREIGN PATENT DOCUMENTS

| EP | 0 071 391 A2 | 2/1983 |
|---|---|---|
| GB | 2 166 232 A | 4/1986 |
| JP | 07/310519 A | 11/1995 |
| JP | 10/115210 A | 5/1998 |
| WO | WO 98/11331 A | 3/1998 |
| WO | WO 2007/140640 A1 | 12/2007 |

\* cited by examiner

DEVICE AND METHOD FOR ASCERTAINING MEASURED VALUES OF GASES AND/OR AN AEROSOL FOR A MACHINE This application claims priority from PCT application No. PCT/EP2012/073017 filed Nov. 19, 2012 which claims priory from European application No. EP 12151046.5filed on Jan. 13, 2012, the disclosures of which are incorporated herein by reference.

TECHNICAL FIELD

The invention relates to a system with measuring devices for determining measured data of gases and/or an aerosol for a machine and to a monitoring method by means of which measured data of gases and/or an aerosol in a machine, in particular measured data of the aerosol concentration in a internal combustion engine, are determined.

BACKGROUND OF THE INVENTION

The monitoring of gases and of aerosol concentrations, particularly of lubricating oil mist in working chambers of internal combustion engines, of fuel high pressure units for supplying internal combustion engines, or of power transmission gears, is of considerable importance in order to avoid damages. A rapid increase of the oil mist concentration is indicative of damages, for example of the tearing off of a lubricating film. As a result of frictional heat thus formed, oil vapors are formed which condensate to oil mist in the working chamber and thus result in a rapid increase of the oil mist concentration. If the resulting hazard is quickly recognized, then explosions and a concomitant threat to persons and further damages to the machine can be prevented with appropriate counteractions such as shutting down of the machine or of individual components of the machine. However, it is also possible to study specific gas components in such a working atmosphere by means of other sensors.

Furthermore, in addition to the tearing off of the lubricating film, so-called blow-throughs may occur between the piston and the associated cylinder wall in bearings of piston engines due to damaged piston rings, which cause a total damage of the piston/cylinder aggregate ("piston seizure"). An increase of the oil mist density with simultaneous rise in temperature due to the hot combustion gases is indicative of such blow-throughs.

First approaches for measuring the oil mist concentration are known from EP-A-0 071 391. In EP-A-0 071 391 it is suggested to draw the aerosol from the working chamber through a measuring compartment by means of a blower and to carry out therein a reflection measurement by means of a radiation source and a radiation sensor. The winged wheel blower suggested therein is intended for use with a plurality of compartments arranged parallel to each other.

The disadvantages of such an arrangement were already shown in WO-A-98/11331. In addition to the considerable constructive and operating requirements of such arrangement, the use of a blower for drawing out has been found to be insufficient, meaning that such a solution should be avoided. Moreover, the drawing out operation also draws waste air through the pipe system, and thus oil deposits in the form of oil bags can form which clog the pipelines and thus render the operation of the measuring device difficult or impossible.

In contrast thereto, in DD-A-239 474 and in GB-A-2 166 232 it is suggested to arrange, for each working chamber of the driving unit of an internal combustion engine, a sensor unit directly in the interior of the respective working chamber and to connect it via an optical or electrical transmission path to an evaluation unit arranged outside of the internal combustion engine. However, such a solution is associated with the disadvantage that the base concentration of oil mist and splash oil in the long run contaminates the sensors and, therefore, also leads to false alarms.

In contrast, in the already mentioned WO-A-98/11331 it is suggested to provide, in each working chamber to be monitored, a sensor unit with an extraction based on a venturi nozzle. Such a measuring device operates without mechanically moved parts and is, therefore, almost wearless. Something similar is also known from JP 7/310519 A. From this, and previously already from DE 26 08 390 A1, it is also already known that an optical measuring path that comprises an optical emitter and an optical receiver may be provided with a so-called curtain by means of which the above mentioned optical elements are kept as free as possible from oil mist deposits etc. This has been previously achieved in such manner that a fresh air flow was generated perpendicular to the optical measuring path in each case in the vicinity of the optical elements. However, this is complex in comparison with the effect.

Moreover, it has been found to be a disadvantage of the device according to WO-A-98/11331A that the energy expense of the venturi pump for drawing in the aerosol mixture from the driving chamber through the optical measuring path is very high, particularly when the optical measuring path is arranged in a casing that is connected with the venturi pump via a pipeline.

SUMMARY OF THE INVENTION

It is an object of the invention to provide an improved system with measuring devices of the above mentioned type for determining measured data of a gas and/or aerosol for a machine. In particular, the expense and here particularly the energy expense should be kept smaller than in the prior art.

This object of the invention is achieved by a measuring device whereby the measures of the invention initially have the result that the required compressed air flow is significantly reduced as compared to the prior art. However, a particular advantage of the mentioned measures of the invention is the possibility of a very compact construction. Moreover, it has been found that with the measures of the invention much better results can be achieved than with the measuring devices according to the prior art.

It is advantageous if the optical sensor unit is configured in such manner that the optical passage between the optical emitter and the optical receiver is laterally displaced with respect to the outlet direction of the compressed air nozzle. In this case an optimal amount of driving chamber gas (aerosol mixture) being drawn out is detected with the optical beam, while the major amount of passing compressed air that is only used for driving, that is for drawing out the driving chamber gas, is conducted past he measuring path without having a significant impact on the measurement.

In order to keep the optical elements free of oil mist deposits, it is advantageous if the sealing air nozzles are arranged and configured in such manner as to allow for a further air flow each from a respective optical emitter and from a respective optical receiver towards the mixing chamber of the compressed air and the extraction atmosphere. In this manner a countercurrent to the possible undesired diffusion direction of the oil mist is generated. This countercurrent is sufficient to prevent any deposits on the optical elements without great expense. With this measure it is possible to avoid the complex "curtain". The sealing air nozzles and accordingly the said countercurrent can possibly be operated merely by the fact that the compressed air feed from the compressed air nozzle also operates this countercurrent. However, the sealing air nozzles are usually operated from a junction of the pressure line.

The measuring device according to the present invention is particularly advantageous if the drawing off from the engine compartment can be interrupted and replaced by a fresh air feed, preferably by means of a valve device. In this case an absolute measurement can be performed if the valve—preferably a magnet valve is closed off before the venturi nozzle and the measuring channel is flushed with fresh air.

A second aspect of the present invention relates to carrying out the measurement with the present measuring device.

The aforementioned elements as well as those claimed and described in the following exemplary embodiments, to be used according to the invention, are not subject to any particular conditions by way of exclusion in terms of their size, shape, use of material and technical design, with the result that the selection criteria known in the respective field of application can be used without restrictions.

BRIEF DESCRIPTION OF THE DRAWINGS

Further details, advantages and features of the object of the present invention will become apparent from the following description and the corresponding drawings, in which measuring devices according to the present invention are illustrated by way of example. In the drawings there is shown in.

DESCRIPTION OF THE PREFERRED EMBODIMENTS

Figure 1:
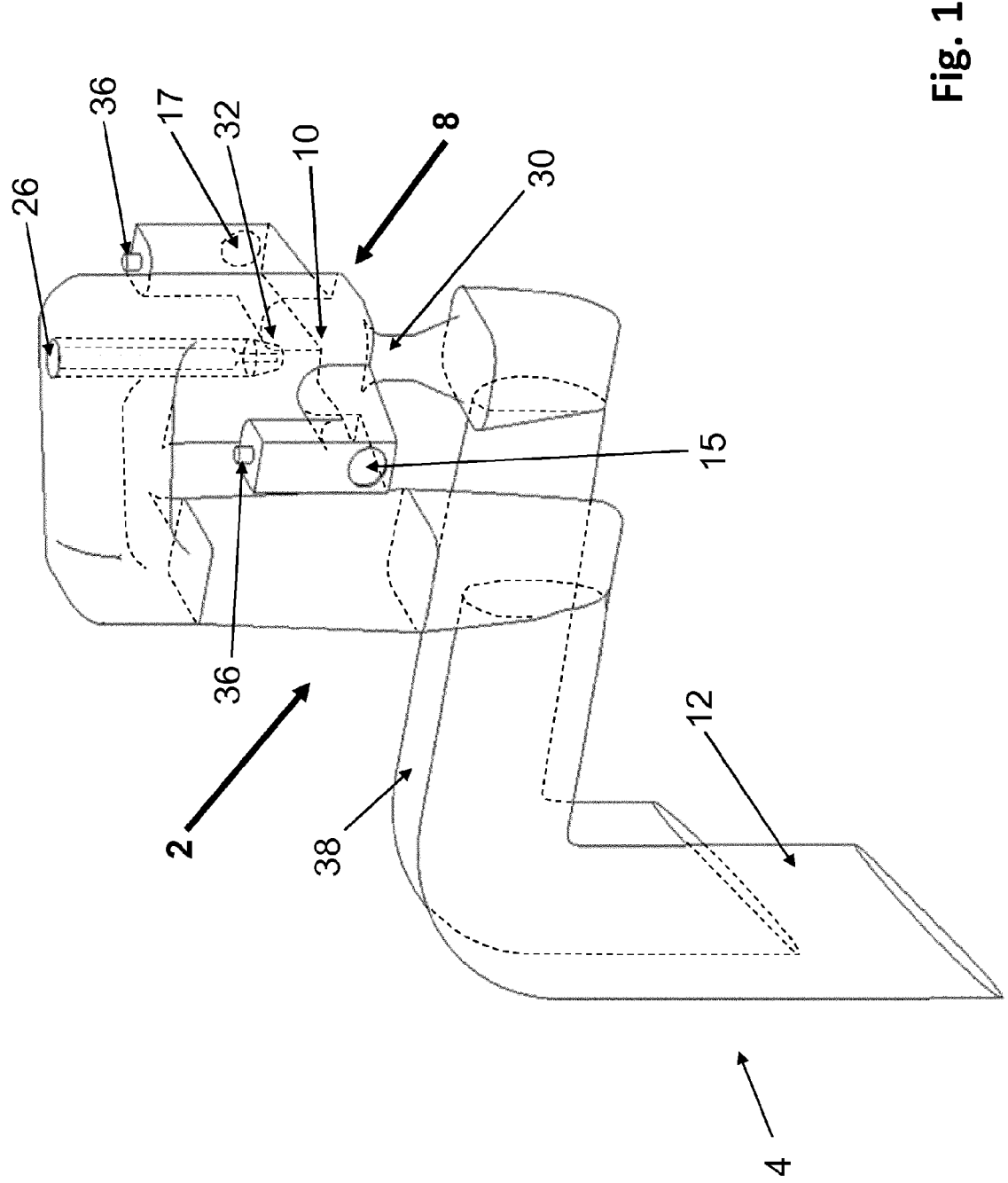
FIG. 1 in a schematic, perspective view, a measuring device on the working chamber of an internal combustion engine, according to a first exemplary embodiment of the present invention, and FIG. 2 a view of the shifters of the pressure supply in the measuring device according to FIG. 1.

FIG. 1 shows a measuring device 2 with its casing releasably arranged to a working chamber 4 of a machine. In the present example, the machine is an internal combustion engine such as a piston engine, for example a diesel engine. The measuring device is used for determining measured data of an aerosol, here of the oil mist in the working chamber of the machine. The measuring device 2 comprises a compressed air jet pump 8 as suction means, the underpressure region 10 of which is in contact with the interior of the working chamber 4 via a suction line 12 through an opening in the wall of the working chamber. Perpendicularly to the outlet direction of the compressed air nozzle 32 and, thus, also substantially perpendicularly to the axis between the compressed air nozzle 32 and the center of the funnel 30 there is configured a light channel, at one end of which there is arranged a light emitter 15 and at the other end of which there is arranged a light receiver 17 of a sensor unit for determining the measured data of the oil mist. The sensor unit comprises an electronics module. In the present exemplary embodiment the light beam of the light emitter 15 is directed towards the light receiver 17, with the light beam passing through the underpressure region of the compressed air jet pump, perpendicularly, but slightly laterally displaced to the outlet direction of the compressed air nozzle and, therefore, also substantially perpendicularly to the axis between the compressed air nozzle 32 and the center of the funnel 30.

The compressed air jet pump 8 is cooperatively connected with a compressed air feed 26 that leads into the compressed air nozzle 32 which blows the compressed air jet into a funnel 30 and thereby generates an underpressure in the underpressure region 10 surrounding the transition region between the compressed air nozzle 32 and the funnel 30. The suction line 12 is connected to the underpressure region 10. In the present exemplary embodiment the outlet direction of the compressed air nozzle 32 is oriented approximately towards the center of the funnel 30.

To the compressed air feed 26 there is connected a junction line 106 that leads into the sealing air nozzles 36. One of the sealing air nozzles is arranged in the vicinity of the light emitter 15 and the other sealing air nozzle is arranged in the vicinity of the light receiver, and compressed air exits from both sealing air nozzles 36 and flows to the venturi arrangement consisting of the compressed air nozzle 32 and the funnel 30 and is fed back into the engine compartment together with the compressed air exiting from the compressed air nozzle 32 by means of the return channel 38 that is configured as feedback line. This arrangement effectively prevents the oil mist possibly escaping from the suction line 12 from reaching the light emitter 15 or the light receiver 17 and polluting them. Such an arrangement has proven to be more effective than the formerly known "curtain solution".

It should be mentioned at this point that the optical arrangement that is configured in the present exemplary embodiment with a light emitter 15 arranged at one end of the light channel and a light receiver 17 arranged at the other end of the light channel may be configured almost equivalently effective if both the light emitter 15 and also the light receiver 17 are arranged at one end of the light channel, and at the other end of the light channel there is arranged a reflector (e.g. a mirror) that is oriented in such manner that the light beam from the light emitter 15 is reflected to the light receiver 17, preferably passing each time through the underpressure region and oriented perpendicularly, but slightly laterally displaced from the outlet direction of the compressed air nozzle and therefore also substantially perpendicular to the axis between the compressed air nozzle 32 and the center of the funnel 30.

Moreover, it should be mentioned that while in the present exemplary embodiment a light beam in the frequency range of the near infrared (860 nm) is provided for use, one may also use wavelengths in the entire spectrum, from infrared to ultraviolet, or a mixture thereof.

The electronic module of the sensor unit is connected for example via a line to an external evaluation unit which displays the measured oil mist concentration. If the oil mist concentration exceeds a predefined threshold value that is indicative of a defect in the driving machine, then a corresponding alarm signal can be released or the machine can be stopped.

Figure 2:
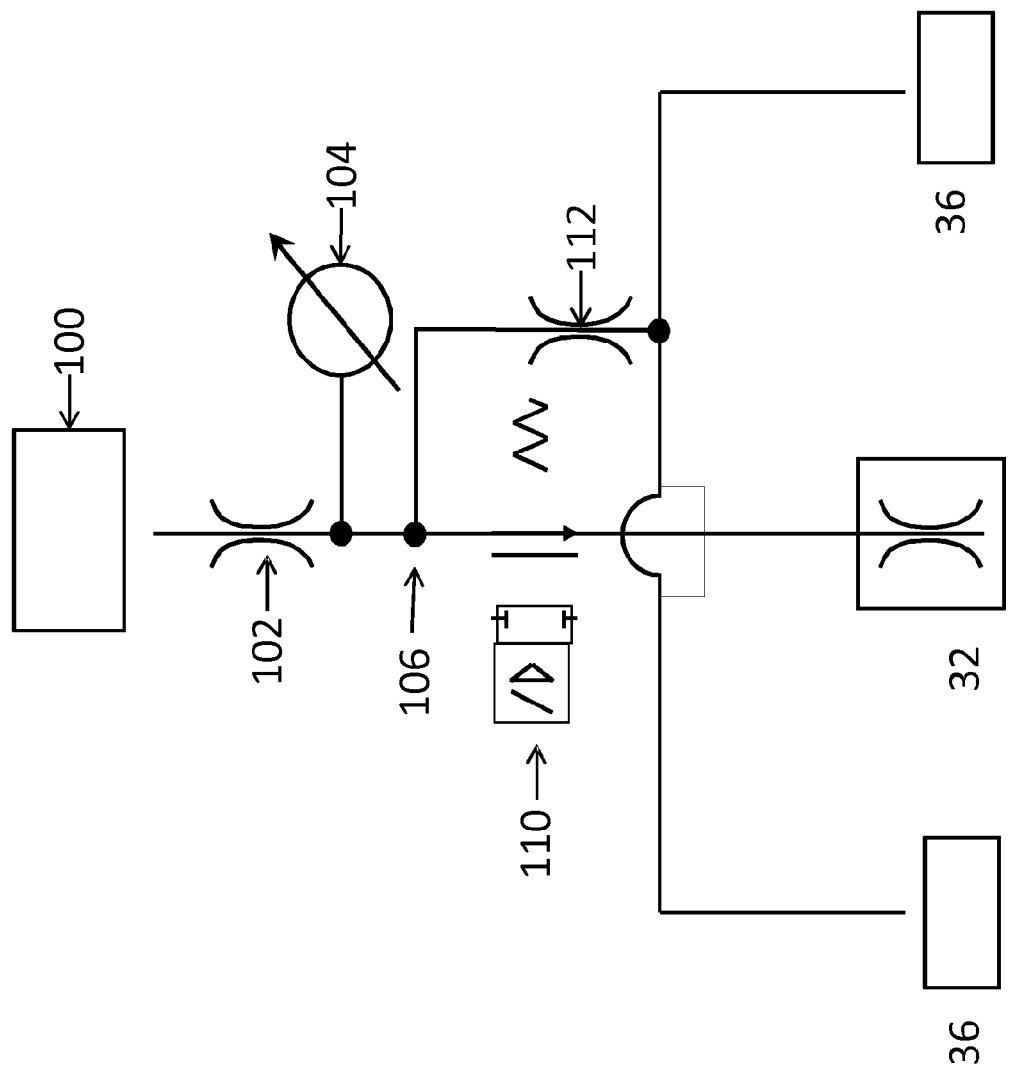

The pressure supply of the present exemplary embodiment is shown in FIG. 2. The pressure supply 100, with a pressure of 3,0 bar in the present exemplary embodiment, provides a volume flow rate of 100 l/h by means of the main throttle 102 with a diameter of 022 mm. A pressure sensor 104 is arranged between the main throttle 102 and the magnet valve 110 and the sealing air throttle 112 for monitoring the pressure supply and thus the volume flow rate being established through the compressed air nozzle 32 and the sealing air nozzles 36. The main branch is led via a magnet valve 110—in the exemplary embodiment with a diameter of 0.45 mm—to the compressed air nozzle 32, which provides a volume flow rate of the compressed air nozzle 32 being 66 l/h. The sealing air branch is led via a sealing air throttle 112 having a diameter of 0.26 mm uniformly to the two sealing air nozzles 36 each of which is provided with an air flow of 17 l/h.

Under normal operating conditions of the measuring device of the exemplary embodiment described above, compressed air flows from the pressure supply 100 through the main throttle 102 both through the opened magnet valve 110 and through the compressed air nozzle 32, thus generating an underpressure carrying off the engine atmosphere, and also flows through the sealing air throttle 112 through the sealing air nozzles 36, thus generating a countercurrent from the optical elements to the funnel 30 protecting the optical elements 15 and 17.

When operating under calibration conditions, however, the magnet valve 110 is closed and the main current through the compressed air nozzle 32 is interrupted. The optical channel between the optical elements 15 and 17 is cleaned by the sealing air nozzles 36, and the measuring device can be subjected to an absolute measurement of the light transmission. This process may be scheduled, for example, once daily and allows for the adjustment of the above mentioned threshold value, because in this manner the measurement can be carried out independently from the emission power of the emitting element 15 and the sensitivity of the light receiver 17 and also from further interfering effects.

It should be pointed out that by virtue of the pressure sensor 104 the above described arrangement is capable of monitoring the functioning of all of the before mentioned nozzles by measuring the absolute pressure and comparing with the target pressure of the respective configuration, thus allowing to readily detect errors both in any of the sealing air nozzles 36 as well as in the two sealing air nozzles.

LIST OF REFERENCE NUMERALS 2 measuring device for determining measured data for an aerosol in the
4 working chamber
8 suction means/compressed air jet pump
10 underpressure region
12 suction line
15 optical emitter
17 optical receiver
26 compressed air feed
30 funnel
32 compressed air nozzle
36 sealing air nozzles
38 return channel
100 pressure supply
102 main throttle
104 pressure sensor
106 junction
110 magnet valve
112 sealing air throttle

The invention claimed is:

1. A measuring device for determining measured data for an aerosol in the working chamber of a machine with a suction means that draws out an aerosol air mixture from the working chamber of the machine and feeds the same to an optical sensor unit having at least an optical emitter and at least an optical receiver, and with an electronic device for operating the optical sensor unit, wherein the suction means is configured as a compressed air jet pump with a compressed air feed, a compressed air nozzle, a pressure discharge channel and an underpressure region, the compressed air nozzle having an outlet direction which is oriented substantially in the direction of the pressure discharge channel, the compressed air feed being connectable to a compressed air source, and a suction line that is connectable to the working chamber of the machine being connected to the underpressure region, characterized in that
the optical sensor unit has an optical passage between the optical emitter and the optical receiver which is oriented substantially perpendicular to the outlet direction of the compressed air nozzle and leads through the underpressure region.

2. The measuring device according to claim 1, characterized in that a suction from an engine compartment is interrupted and replaced by a fresh air feed, by means of a valve device.

3. A method for determining measured data for an aerosol in the working chamber of a machine by means of a measuring device according to claim 2, wherein an aerosol air mixture is drawn out from the working chamber of the machine and fed to the optical sensor unit having at least an optical emitter and at least an optical receiver, and which has an electronic module for operating the optical sensor unit, the compressed air feed being connected to a compressed air source, and a suction line connected to the working chamber of the machine being connected to the underpressure region, characterized in that
a light beam in the frequency range within, below or above the visible range, or with a mixture thereof, is emitted, by means of the optical sensor unit, from the optical emitter to the optical receiver, the light beam being oriented substantially perpendicular to the outlet direction of the compressed air nozzle, and being guided through the underpressure region.

4. A method for determining measured data for an aerosol in the working chamber of a machine by means of a measuring device according to claim 1, wherein an aerosol air mixture is drawn out from the working chamber of the machine and fed to the optical sensor unit having at least an optical emitter and at least an optical receiver, and which has an electronic module for operating the optical sensor unit, the compressed air feed being connected to a compressed air source, and a suction line connected to the working chamber of the machine being connected to the underpressure region, characterized in that
a light beam in the frequency range within, below or above the visible range, or with a mixture thereof, is emitted, by means of the optical sensor unit, from the optical emitter to the optical receiver, the light beam being oriented substantially perpendicular to the outlet direction of the compressed air nozzle, and being guided through the underpressure region.

5. The method according to claim 4, characterized in that a further air flow is led by means of sealing air nozzles from a respective optical emitter and from a respective optical receiver to the underpressure region, wherein compressed air is guided from a respective junction line to the sealing air nozzles.

6. The method according to claim 4, characterized in that the light beam between the optical emitter and the optical receiver is laterally displaced with respect to the outlet direction of the compressed air nozzle.

7. The method according to claim 6, characterized in that a further air flow is led by means of sealing air nozzles from a respective optical emitter and from a respective optical receiver to the underpressure region, wherein compressed air is guided from a respective junction line to the sealing air nozzles.

8. The measuring device according to claim 1, characterized in that the optical sensor unit is configured in such manner that the optical passage between the optical emitter and the optical receiver is laterally displaced with respect to the outlet direction of the compressed air nozzle.

9. The measuring device according to claim 8, characterized in that the suction from the engine compartment is interrupted and replaced by a fresh air feed, by means of a valve device.

10. A method for determining measured data for an aerosol in the working chamber of a machine by means of a measuring device according to claim 8, wherein an aerosol air mixture is drawn out from the working chamber of the machine and fed to the optical sensor unit having at least an optical emitter and at least an optical receiver, and which has an electronic module for operating the optical sensor unit, the compressed air feed being connected to a compressed air source, and a suction line connected to the working chamber of the machine being connected to the underpressure region,
characterized in that
a light beam in the frequency range within, below or above the visible range, or with a mixture thereof, is emitted, by means of the optical sensor unit, from the optical emitter to the optical receiver, the light beam being oriented substantially perpendicular to the outlet direction of the compressed air nozzle, and being guided through the underpressure region.

11. The measuring device according to claim 8, characterized by sealing air nozzles that are arranged and configured in such manner as to allow for a further air flow each from a respective optical emitter and from a respective optical receiver towards the underpressure region.

12. The measuring device according to claim 11, characterized in that the suction from the engine compartment is interrupted and replaced by a fresh air feed, by means of a valve device.

13. The measuring device according to claim 11, characterized in comprising a respective junction line from the compressed air feed to the sealing air nozzles.

14. The measuring device according to claim 13, characterized in that the suction from the engine compartment is interrupted and replaced by a fresh air feed, by means of a valve device.

15. The measuring device according to claim 1, characterized by sealing air nozzles that are arranged and configured in such manner as to allow for a further air flow each from a respective optical emitter and from a respective optical receiver towards the underpressure region.

16. The measuring device according to claim 15, characterized in that the suction from the engine compartment is interrupted and replaced by a fresh air feed, by means of a valve device.

17. A method for determining measured data for an aerosol in the working chamber of a machine by means of a measuring device according to claim 15, wherein an aerosol air mixture is drawn out from the working chamber of the machine and fed to the optical sensor unit having at least an optical emitter and at least an optical receiver, and which has an electronic module for operating the optical sensor unit, the compressed air feed being connected to a compressed air source, an a suction line connected to the working chamber of the machine being connected to the underpressure region,
characterized in that
a light beam in the frequency range within, below or above the visible range, or with a mixture thereof, is emitted, by means of the optical sensor unit, from the optical emitter to the optical receiver, the light beam being oriented substantially perpendicular to the outlet direction of the compressed air nozzle, and being guided through the underpressure region.

18. The measuring device according to claim 15, characterized in comprising a respective junction line from the compressed air feed to the sealing air nozzles.

19. The measuring device according to claim 18, characterized in that the suction from the engine compartment is interrupted and replaced by a fresh air feed, by means of a valve device.

20. A method for determining measured data for an aerosol in the working chamber of a machine by means of a measuring device according to claim 18, wherein an aerosol air mixture is drawn out from the working chamber of the machine and fed to the optical sensor unit having at least an optical emitter and at least an optical receiver, and which has an electronic module for operating the optical sensor unit, the compressed air feed being connected to a compressed air source, and a suction line connected to the working chamber of the machine being connected to the underpressure region,
characterized in that
a light beam in the frequency range within, below or above the visible range, or with a mixture thereof, is emitted, by means of the optical sensor unit, from the optical emitter to the optical receiver, the light beam being oriented substantially perpendicular to the outlet direction of the compressed air nozzle, and being guided through the underpressure region.

* * * * *